United States Patent [19]

Sugden

[11] Patent Number: 4,686,186
[45] Date of Patent: Aug. 11, 1987

[54] RECOMBINANT VECTOR AND EUKARYOTIC HOST TRANSFORMED THEREBY

[75] Inventor: William M. Sugden, Verona, Wis.

[73] Assignee: Wisconsin Alumni Research Foundation, Madison, Wis.

[21] Appl. No.: 654,780

[22] Filed: Sep. 26, 1984

[51] Int. Cl.⁴ .................... C12P 21/00; C12N 7/00; C12N 15/00
[52] U.S. Cl. .................... 435/243; 435/68; 435/70; 435/235; 435/320; 935/6; 935/32; 935/70
[58] Field of Search .................... 435/68, 70, 91, 253, 435/243, 235, 317, 172.3; 536/27; 424/85, 89; 935/32, 57, 71, 74

[56] References Cited

PUBLICATIONS

Yates et al. (1984) *Proceedings National Academy of Sciences USA*, vol. 81, pp. 3806–3810.
Lusky et al. (1984) *Cell*, vol. 36, pp. 391–401.
Stow et al. (1983) *Nucleic Acids Research*, vol. 11, pp. 8205–8220.
Spaete et al. (1982) *Cell*, vol. 30, pp. 395–304.
Pages 1 and 2 of ATCC Quaterly Newsletter (Jul. 1984), (admitted prior art).
R. C. Mulligan et al., 78 PNAS USA 2072–2076 (1981).

*Primary Examiner*—Thomas G. Wiseman
*Assistant Examiner*—Stephanie Seidman
*Attorney, Agent, or Firm*—Quarles & Brady

[57] ABSTRACT

A recombinant vector and a eukaryotic host transformed thereby are disclosed. In one embodiment, there is a eukaryotic host that has a recombinant plasmid comprising a plasmid backbone, a foreign eukaryotic gene component, and a first gene segment from a lymphotrophic herpes virus. There is also provided in the host a second gene segment from a lymphotrophic herpes virus. The first and second gene segments interact to assist the plasmid in maintaining itself as a plasmid when inserted into a eukaryotic host, and permit stable replication of the host. The preferred virus is the Epstein-Barr virus, and the two preferred viral segments are the EBV origin of replication and the segment coding for EBNA protein.

8 Claims, 3 Drawing Figures

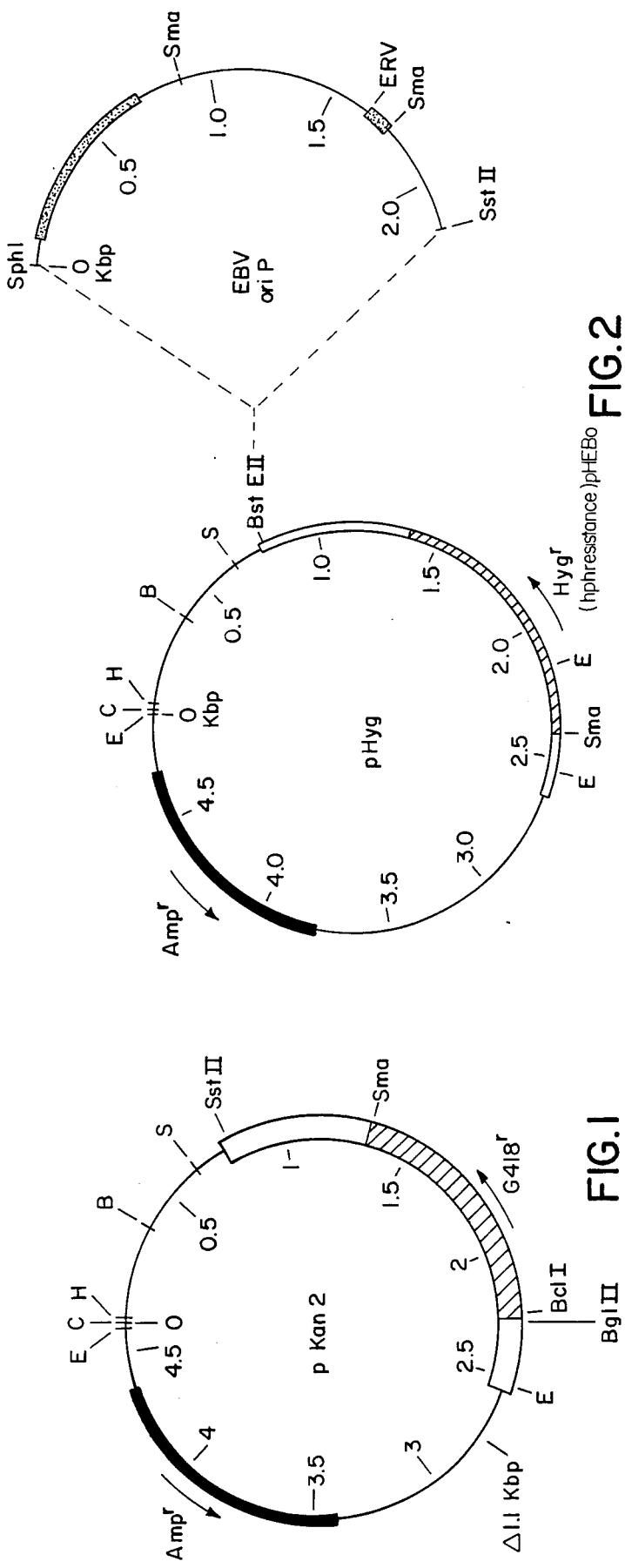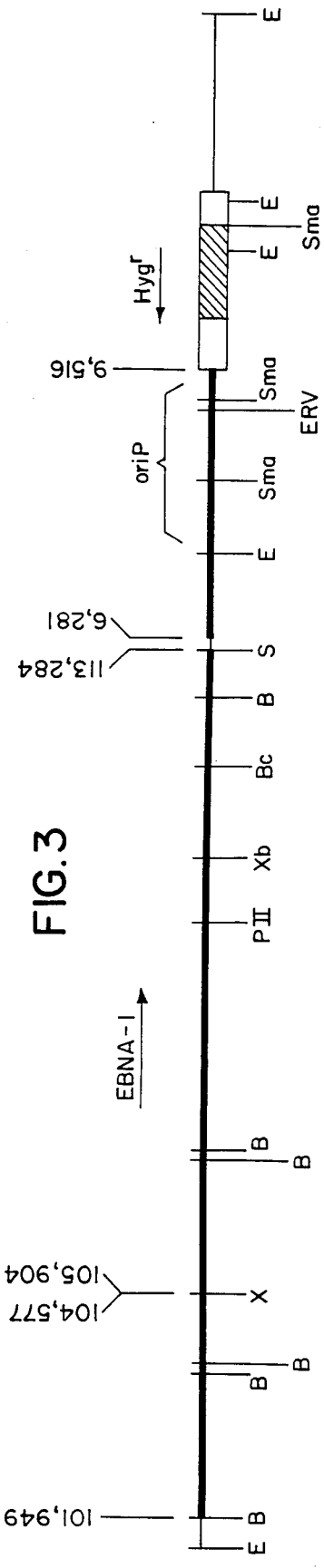

RECOMBINANT VECTOR AND EUKARYOTIC HOST TRANSFORMED THEREBY

This invention was made with U.S. Government support awarded by the National Institute of Health (NIH) under Grant Nos. CA 22443, CA 07175, CA 09135, and CA 09075. The U.S. Government has certain rights in this invention.

BACKGROUND OF THE INVENTION

A. Field of The Invention

The present invention relates to recombinant DNA technology. It is especially useful for allowing stable replication of foreign eukaryotic genes in eukaryotic hosts.

B. Description of The Art

Although much progress has been made in the last decade in using recombinant-DNA techniques with prokaryotic hosts, many important eukaryotic proteins (e.g. plasminogen activator) are not readily expressed in a prokaryotic host. It therefore is desirable to develop recombinant vectors for use with eukaryotic hosts.

Using plasmids as vectors for eukaryotic hosts has been tried, but with only limited success. For example, the SV-40 vector in R. C. Mulligan et al., 78. P.N.A.S. U.S.A. 2072-6 (1981) either replicated too fast and killed the cell or integrated into the cell genome (which led to loss of expression, mutation, and other problems). Some bovine papilloma virus plasmid vectors have also been tried, see ATCC Quarterly News Letter (July 1984), but they have had very limited host ranges (and thus are of very limited commercial value). Thus, it can be seen that there is a need for an improved vector that permits stable replication of eukaryotic DNA in a wide range of hosts.

SUMMARY OF THE INVENTION

One embodiment of the invention relates to a recombinant plasmid vector. There is provided a plasmid backbone, a foreign eukaryotic gene component, and a first gene segment from a lymphotrophic herpes virus. The first gene segment is positioned on the plasmid so that it is capable of assisting in maintaining the plasmid as a plasmid if and when the plasmid is inserted into a eukaryotic host that has been transformed by the lymphotrophic virus. Preferably, the segment is an origin of replication of Epstein-Barr virus, the plasmid backbone is an *E. coli* plasmid segment, and the foreign eukaryotic gene codes for a protein of interest (such as plasminogen activator).

It is also desirable to include an antibiotic resistance gene in the plasmid that the host does not have prior to cloning (so that cells that do not contain the plasmid can be killed by adding the antibiotic). One aspect of the invention therefore involves the addition of a hygromycin B resistance gene to the vector. (Other antibiotic resistance genes, for example, the neomycin phosphotransferase gene of *E. coli*, can be used, too.)

In another preferred form, the recombinant plasmid is provided with a second gene segment from the lymphotrophic herpes virus. The second gene segment normally acts in trans to the first gene segment in the naturally occurring virus. The first and second gene segments assist the plasmid in maintaining the plasmid as a plasmid upon its insertion in a eukaryotic host, even where the cell is not transformed by the virus. Preferably, this trans segment codes for the EBNA protein of EBV.

In yet another form, a eukaryotic host is provided which has a recombinant plasmid with a plasmid backbone, a foreign eukaryotic gene component, and a first gene segment from a lymphotrophic herpes virus. Thee may also be provided a second gene segment from a lymphotrophic herpes virus either as part of the plasmid or by transformation of the host with the virus. The first and second virus gene segments assist in the maintaining of the plasmid as a plasmid. In a preferred form, the host cell is a human B-lymphoblast.

An "origin of replication" can be defined as that part of the genome that assists a lymphotrophic herpes virus in staying as a plasmid while it is in its latent state. In the alternative, it can be defined as the site where DNA synthesis initiates. The claims of this patent which refer to the origin are meant to cover both such definitions.

A "lymphotrophic" herpes virus is a herpes virus that replicates in a lymphoblast (e.g. a human B lymphoblast) and becomes a plasmid for a part of its natural life-cycle. After infecting a host, these viruses latently infect the host by staying as plasmids. The herpes simplex virus (HSV), which is widely used in recombinant technology because of its thymidine kinase gene, is not a "lymphotrophic" herpes virus.

An important aspect of the invention is the realization that there is a discrete gene portion of this class of viruses which permits these plasmids to remain as plasmids, and that these portions could be transferred to other plasmids to provide them with similar characteristics. Another important aspect of the invention is the identification and isolation of these segments in Epstein-Barr virus. Using techniques analogous to those used for EBV, similar regions in other lymphotrophic viruses can be identified, and it may even be possible to locate other EBV regions which perform these functions.

Yet another aspect of the invention is that for Epstein-Barr virus two segments (cis and trans) are required. Thus, one can either position both segments on the recombinant plasmid, or place the cis segment in the plasmid and let the trans segment's protein, EBNA, be supplied by EpsteinBarr virus that has already transformed the cell. Note also that the trans element can be provided by integrating it alone into an appropriate recipient cell. One such eukaryotic host is a cell not transformed by EBV, but which carries the EBNA gene because this gene has been selected to integrate into the host's chromosomes.

Also, for purposes of selection, it is preferred to provide the recombinant plasmid with resistance which EBV transformed lymphoblasts normally do not have. In this regard, hygromycin B readily kills EBV transform lymphoblasts. However, a vector that carries the hph product which inactivates hygromycin B can be efficiently selected on EBV transformed cells.

The objects of the invention therefore include:

A. Providing a recombinant plasmid vector of the above kind which can be used to transform a wide range of eukaryotic cells and permit stable replication and expression thereafter;

B. Providing a eukaryotic vector of the above kind which will permit stable replication of recombinant plasmids in latently infected eukaryotic cells;

C. Providing a eukaryotic host of the above kind which permits stale replication of the plasmid.

These and still other objects and the advantages of the present invention will be apparent from the description that follows. In the description, the preferred embodiments of the invention will be described with reference to the accompanying drawings. These embodiments do not represent the full scope of the invention. Rather, the invention may be employed in other embodiments. Reference should therefore be made to the claims to interpret the breadth of the invention.

BRIEF DESCRIPTION OF THE DRAWING

FIG. 1 depicts the structure of pKan 2, a precursor to pHEBo;

FIG. 2 depicts the structure of pHEBo, a plasmid containing the cis component from Epstein-Barr virus; and FIG. 3 depicts the plasmid p174, a plasmid containing both the cis and trans Epstein-Barr virus components.

DESCRIPTION OF THE PREFERRED EMBODIMENTS

General Overview

Epstein-Barr virus (EBV) transforms human B-lymphocytes into proliferating blasts that are efficiently established into cell lines. The viral DNA in these cell lines is usually present as complete, unintegrated plasmid molecules. I have identified a cis-acting element of EBV, which I have named oriP, that permits plasmid maintenance when one other viral function that I have found is provided in trans. I have also discovered that the trans function produces a protein previously know as EBNA.

Also, hygromycin B readily kills EBV-transformed lymphoblasts. Thus, I have made my vectors so that they carry both oriP and express the hph product which inactivates hygromycin B. These vectors can therefore be efficiently selected.

In R. Baer et al., 310 Nature 207–211 (1984), the authors provide a genetic sequence and numbering code for Epstein-Barr virus's 172 kbp. I have discovered that the cis component is located within nucleotide number 7333 to 9516, and I have learned that the trans component is located within nucleotide number 107567 to 110176.

In my article J. Yates, N. Warren, D. Reisman, and B. Sugden, 81 P.N.A.S. U.S.A. 3806–3810 (1984) (not prior art), I describe how the cis component was isolated using a test vector pKan 2 (see FIG. 1). (The disclosure of this article and of all other articles cited herein are incorporated herein as if fully set forth). Essentially what I did was to clone various segments of the viral DNA into a selectable vector until I found the regions that provided the replication as a plasmid in cells providing stable function(s) needed in trans.

I then constructed a vector which I call pHEBo (see FIG. 2) that contains the oriP element of EBV and also the hph gene. The hph gene was isolated from *E. coli* and inserted between the promoter and poly A addition signals of the herpes simplex virus thymidine kinase (HSV-1 TK) gene.

I find that the pHEBo vector gives up to $10^5$ more resistant colonies per microgram of DNA than does a related vector lacking oriP. Also, among the cells surviving the attempt to introduce DNA up to 3% also survive selection to grow as resistant colonies, and the resistant colonies usually carry ten plasmid copies of pHEBo per cell but can carry between one and sixty copies per cell. This vector is useful in introducing DNAs stably into EBV-transformed cells. Finally, as described below, I created a vector p174 (FIG. 3), which had both the cis and trans EBV segments, and then transformed a wide variety of eukaryotic hosts with this vector.

Materials and Methods

Antibiotics.

The derivative of neomycin, G418, was purchased from Gibco and made as a stock solution at 100 mg per ml in PBS. Hygromycin B was purchased from Calbiochem and made as a stock solution at 10 mg per ml in PBS and brought to $3.5 \times 10^{-2}$ M with glacial acetic acid to neutralize the solution. We found that the active half-life of solutions of hygromycin B at 4° C. is on the order of 10 days indicating that their shelf-life as a solution is limited.

Cells.

Human lymphoblastoid cell lines were propagated in RPMI 1640 plus 10% fetal bovine serum. Another test line that we tried, the cotton top marmoset cell line, B95-8, was propagated in RPMI 1640 plus 5% calf serum.

Introduction Of DNAs Into Cells.

Two methods were used. The first was that of protoplast fusion (W. Schaffner et al. 77 P.N.A.S. U.S.A. 2163-7 (1980) and R.M. Sandri-Goldin et al. 1 Mol. Cell. Biol. 743-752 (1981) in which protoplasts carrying the desired plasmid vector which had been amplified using chloramphenicol were mixed with the recipient cells at a ratio of 1000:1, spun into a pellet, and fused with 50% polyethylene glycol in MEM for one minute at 37° C., slowly mixed for one minute, diluted to 20 mls with MEM over four minutes, spun out and distributed to 24 well plates at anywhere from 10 to $3 \times 10^5$ viable cells per well. Between 1 to 20% of the recipient cells survived the fusion 24 hours later. Selective medium was added to each well 24 to 48 hours later.

The second method used for DNA introduction was electroporation (E. Newmann et al. 1 Embo. J. 841-845 (1982)). Cells ($0.5-2 \times 10^7$) in PBS (0.5 ml) containing 5-10 microgram of plasmid DNA were exposed at 0° C. between electrodes separated by 1 centimeter to a transient current of 3-6 amps (the rise time was less than 1 microsecond; the time constant for the decay was approximately 30 milliseconds) using an Isco 494 power source. Between 1 and 40% of the recipient cells survived electroporation 24 hours later. After 24 to 48 hours, cells were distributed to 24 well plates at anywhere from 10 to $3 \times 10^5$ viable cells per well in selective medium.

Recombinant DNA And DNA Analysis.

Plasmid DNAs were constructed using standard techniques. Plasmid DNAs in resistant lymphoblasts were analyzed either after selective extraction using the method of Hirt (see 26 J. Mol. Biol. 365-369 (1967)), or from total cell DNA. The method of Southern (see 98 J. Mol. Biol. 503-517 (1975)) was used to detect the plasmid DNAs and in all cases the probe used was the DNA of pHyg (FIG. 2) that had been labelled by nick translation. The signals in Southern transfers were quantified by cutting out the appropriate bits of nitrocellulose identified using an autoradiograph as a template and counting them in a liquid scintillation counter.

Construction of pKan 2 and pHEBo

Plasmid pHEBo is derived from pHyg and the cis EBV oriP fragment. pHyg is in turn derived from pKan 2 and pLG89. Plasmid pLG89 was constructed by Gritz and Davies as described in 25 Gene 179–188 (1983). The synthesis of pKan 2 is reported in my article J. Yates, N. Warren, D. Reisman, and B. Sugden, 81 P.N.A.S. U.S.A. 3806–3810 (1984) (not prior art). Its structure is depicted in FIG. 1.

In FIG. 1, the pBR322 (from *E. coli*) portion of pKan 2 (thin and thick single lines) was constructed by replacing the simian virus 40 origin of pSVod (see P. Mellon et al. 27 Cell 279–288 (1981)) with the 31-bp EcoRI to HindIII fragment of pBR322. A 1.1-kbp deletion, which removes the "poison sequence" (see M. Lusky, 293 Nature (London) 79–81 (1981)) is also shown.

Also in FIG. 1, resistance to G418$^r$) is provided by positioning the gene encoding aminoglycoside phosphotransferase II of the bacterial transposon Tn5 (hatched box) between the regions of transcription initiation and termination of the herpes simplex virus-1 (HSV-1) TK gene (open boxes) as first described in F. Colbere-Garapin et al. 150 J. Mol. Biol. 1–14 (1981). This was done by inserting between Nae I sites at pBR322 positions 770 and 1284 the Pvu II fragment of HSV-1 containing the TK gene (see S.L. McKnight, 8 Nucleic Acids Res. 5949–5964 (1980)) and inserting between the Bgl II and Sma I sites of the HSV sequences the Bgl II to Sma I fragment of Tn5, which encodes drug resistance (see R.A Jorgensen, et al., 177 Mol. Gen. Genet. 65–72 (1979)). Cleavage sites are shown for endonucleases EcoRI, E; Cla I, C; HindIII, H; BamHI, B; Sal I, S; Sma I, Sma; as well as Sst II, Bcl I, and Bgl II. To form pHyg, pKan 2 was then digested with SmaI and BglII to remove the G418$^r$ sequences derived from Tn5.

The hph gene was isolated from *E. coli* as reported in Gritz and Davies, 25 Gene 179–188 (1983) and inserted in pLG89 with Bam HI linkers, the linker use being reported therein. The hph gene was inserted into the digested pKan2 using blunt-end ligation at the SmaI site, and "sticky-end" ligation at the BglII site. The SmaI and BglII sites of pKan2 were lost during ligation.

The final cis segment containing plasmid, pHEBo, (which confers resistance to hygromycin B, carries EBV oriP, and replicates as a plasmid in EBV-transformed cells) was constructed from pHyg and a plasmid carrying the BamC fragment of EBV. pBamC is identified and is contructed as described in J. Yates, N. Warren, D. Reisman, and B. Sugden 81 P.N.A.S. U.S.A. 3806–3810 (1984) (not prior art). pHyg was digested with BstEII and its ends repaired. pBamC was digested with SphI and SstII and the fragment mapping from 7333 to 9516 bp on the EBV map cited at Baer et al. 310 Nature 207–211 (1984) which carries oriP was isolated, and its ends repaired with T4 DNA polymerase. The EBV DNA was then blunt-end ligated into the digested pHyg to yield pHEBo. The BstEII, SphI, and SstII sites were all lost in this process.

Shown in FIG. 2 are relevant endonuclease sites: E, EcoRI; C, ClaI; H, HindIII; ERV, EcoRV; B, BamHI; S, SalI; BstEII; Sma, SmaI; SphI; SstII. The thickened single line indicates the beta-lactamase gene of pBR322; the open boxes indicate the regions carrying the promoter and poly A addition signals derived from the HSV-1 TK gene; the hatched box indicates the hph gene of *E. coli* which encodes resistance to hygromycin B; and the stippled boxes indicate two subregions of EBV DNA which are both required for cis oriP function.

Preparation of Hosts

The two plasmids, pHyg (as a control) and pHEBo, were then introduced into different EBV-transformed lymphoblasts using protoplast fusion and electroporation as described above, and survivors to hygromycin B selected. To ensure that the lymphoblasts did assimilate DNA at least transiently, SV40 DNA was introduced into cells using electroporation and the cells stained for SV40 T-antigen 36 hours later. In this experiment 17% of the cells survived electroporation and 4–5% of the survivors expressed T-antigen indicating that this case minimally 4–5% of the survivors take up the added DNA. Among the cells exposed to the control pHyg, none became resistant to hygromycin B (indicating that this control plasmid is not maintained and expressed efficiently in these cells.) At least 2 to 3% of cells exposed to pHEBo, on the other hand, proliferated and were resistant to hygromycin B. The combination of the hph gene of *E. coli* encoding resistance to hygromycin B and the oriP element of EBV in a vector permits that vector to be selected efficiently in EBV-transformed cells.

The high efficiency with which pHEBo can be selected to replicate as a plasmid in EBV-transformed cells indicates that it can provide an easy route to cloning eukaryotic genes. When the gene's product is expressed upon cloning and can be selected or screened for, then cloning a library of the foreign eukaryotic genome into pHEBo, e.g. at the ClaI, Hind III, Bam H1, and Sal 1 sites of pHEBo, introducing it into an EBV-transformed lymphoblast, selecting the hygromycin B-resistant colonies, and selecting or screening among them for the desired gene product should yield either the gene itself or one that induces its expression now cloned into the plasmid pHEBo.

A culture of *E. Coli* DH1 cells containing pHEBo is on deposit at the American Type Culture Collection, Rockville, Md. with ATCC number 39820. It will be made available upon issuance of this patent and as provided. under U.S. and other applicable patent laws. However, this availability and the availability of the other deposit described herein is not to be construed as a license to use the invention.

Construction of Cis plus Trans Plasmid p174

I have discovered that the trans-acting gene that assists oriP function in EBV is the gene that encodes EBNA-1 (Epstein-Barr virus nuclear antigen). The repetitive portion of this gene encoding about one-third of EBNA-1 is dispensible for supporting oriP function. Circular DNAs that carry oriP, the EBNA-1 gene, and a selectable marker replicate autonomously in cells derived from at least four lineages and three species. One such plasmid I created is p174 (see FIG. 3). With this vector, EBV-transformation is not required. This is advantageous where EBV contamination is a concern.

To map the gene of the proposed trans-acting function, overlapping segments of the EBV genome were first individually integrated into the genome of the human thymidine kinase (TK)-negative cell line using a set of G418-selectable, recombinant plasmids. See generally J. Yates et al., supra (not prior art) for analogous techniques. The derived cell lines were then co-transfected with the HAT-selectable control plasmid pΔπTK or in the alternative with a plasmid carrying oriP (e.g.pTK BamC as reportedin J. Yates et al.).

Cells into which the appropriate plasmid had been integrated could be transfected with the oriP bearing plasmids five to thirty times as efficiently as with the vector pΔπTK. Analysis of DNA from the HAT-resistant clones showed that the cell lines that were efficiently transfected by pTKBamC maintained pTKBamC as a plasmid at two to four copies per cell. Integrants carrying all other regions of the EBV genome showed no increase in transfection frequency dependent on oriP and did not maintain pTKBamC as a plasmid. These results imply that the EBV DNA that spans BamHl Z to SalI F (Baer coding) encodes the proposed trans-acting product that allows efficient transfection and maintenance of oriP-bearing plasmids.

A variety of studies indicate that the Epstein-Barr nuclear antigen EBNA-1 is encoded within the BamHl K fragment, which lies within the SalI F fragment of EBV DNA. See W. P. Summers, et al., 79 P.N.A.S. U.S.A. 5688–5692 (1982); K. Hennessy, et al., 220 Science 1396–1398 (1983); K. Hennessy, et al., 80 P.N.A.S. U.S.A. 5665–5669 (1983). A 2.9 kbp BamHl to HindIII subfragment of BamHl K encodes most, if not all, of the EBNA-1 polypeptide. D. Fischer et al., 81 P.N.A.S. U.S.A. 43–47 (1984); R. Baer et al. 310 Nature 207–211 (1984).

I therefore constructed a G418-selectable plasmid containing the 2.9 kbp subfagment of BamHl K and the transcriptional enhancer of SV40. This plasmid was then integrated into several cell clones using Ca++ mediated transfection. F. L. Graham & A. J. Vander Eb. 52 Virology 456–467 (1973). Two of five such cell lines expressed levels of EBNA-1 that could be detected by anticomplement immunofluorescence. The same two clones, could be transfected at high efficiency with pTKBamC giving rise to clones carrying one to five replicating copies of the oriP-bearing plasmid per cell.

Thus, the trans function required by oriP maps within the 2.9 kbp region that also encodes EBNA-1. In other experiments, the SV40 enhancer was found to be required for efficient expression of function from the integrated 2.9 kbp fragment. This finding is consistant with evidence that the mRNA for this region is a 3.7 kb transcript beginning upstream of BamHl K. V. van Santen, et al. 78 P.N.A.S. U.S.A. 1930–1934 (1979); M. Heller, et al. 44 J. Virol. 311–320 (1982).

Between the BamHl to PvuII sub-fragment of Bam H1K lies an open reading frame termed BKRFl by Baer et al. (supra) that is the correct size to encode the EBNA-1 polypeptide. About one third of this open reading frame is a repetitive sequence of glycine and alanine codons that has been shown to encode part of EBNA-1 (K. Hennessey (2 articles) supra). A spontaneous deletion of this repetitive region was obtained from a recombinant bacteriophage clone grown in recA+ E. coli. See G. Buell, et al. 40 J. Virol. 977–982 (1981). A plasmid which carries this deletion was fully functional, indicating that most or all of the triplet repeats are dispensable for the replication function of EBNA-1.

I do not infer from these experiments that transcription of the EBNA-1 gene on any of the described plasmids occurs as it does from the viral genome. If the EBNA-1 gene is placed on pHEBo in the opposite orientation to shown in FIG. 3, it fails to function unless a transcriptional enhancer is provided. The efficient expression of function obtained with plasmids may depend on a promotor(s) present on pHEBo, perhaps on one of those found near the bacterial ampicillin resistance gene.

The ability of plasmids carrying both oriP and the EBNA-1 gene to replicate in human D98/AH2 cells (derived from HeLa cells, of epithithial origin), in Ma134 African green monkey kidney cells, and in D17 dog fibrosarcoma cells has been shown. In addition to the human, monkey, and dog cell lines, these plasmids were found to be maintained in Wilson cells, an EBV-negative, human B-lymphoma cell line, and in K562 cells, a human erythroleukemia cell line.

The wide host range for stable plasmid replication of the EBV-derived plasmids is in marked contrast to the replication of plasmids derived from bovine papilloma viruses. Such plasmids have not been reported to replicate in cells other than from two mouse cell lines and one rat cell line.

Plasmids constructed to carry oriP, the EBNA-1 gene, and a selectable marker replicate autonomously as "mini-EBV" plasmids in a variety of cultured cells. One such plasmid, p174, is constructed from the pHyg.

As shown in FIG. 3, the portion of EBV DNA which contains oriP in p174 is larger than that in pHEBo. It spans sequences 6281 to 9516 on the EBV map (Baer et al.) and is inserted into the Bst E II site of pHyg. The EBV DNA which contains the gene encoding EBNA-1 is inserted between the Bam H 1 site and the Sal 1 sites, thus deleting the prokaryotic DNA sequences between those sites. The EBV DNA inserted at the Bam Hl site in p174 begins with nucleotide number 101949 (which is a Bam H 1 site in the viral DNA) and continues to nucleotide number 104577 which is an XhoI site in the viral DNA.

The viral DNA between this XhoI site and the next one in the DNA sequence at nucleotide number 105904 is not present in p174. The viral DNA from nucleotide number 105904 to 113284 is contained in p174 and is positioned between the XhoI site (nucleotide number 104577) and the Sal 1 site. The plasmid is 17.7 kilobase pairs in size, contains the cis- and trans- acting elements of EBV that permit it to replicate as a plasmid in a variety of mammalian cells, and confers resistance to hygromycin B.

The plasmid 174 is represented in FIG. 3 by a line in which the circular DNA has been linearized at the Eco R1 site in the pBR322 DNA. The numbers above the line give the nucleotide numbers of the EBV DNAs (thickened lines) in p174. The nucleotide numbers are taken from Baer et al. 310 Nature 207–211 (1984). The thin lines represent sequences derived from pBR322. The open boxes represent promoter and poly A addition signals derived from the HSV-1 TK gene and the hatched box contains sequences encloding the hygromycin B phosphotransferase gene derived from *E. coli*. Shown are relevant endonuclease sites: E, EcoRl; B, BamHl; X, Xho1; PII, PvuII; Xb, XbaI; Bc, Bcl I; S, Sal 1; Sma, SmaI; ERV, EcoRV. There are multiple Pvu II sites not shown; the one that is shown indicates the extent of the minimal DNA from the Bam H 1 site required for EBNA-1 function.

A culture of p174 in *E. coli* DH1 is deposited with American Type Culture Collection in Rockville, Md. with ATCC. #39819 under the same condition as for pHEBo. Cloning of p174 is achieved using techniques analogous to those previously described.

It will thus be appreciated that the present invention allows one to stably replicate eukaryotic genes in eukaryotic cells. While we suggest plasminogen activator as a suitable gene candidate, the claims are meant to cover numerous other eukaryotic genes of interest. Further, while a *E. coli* "plasmid backbone" was chosen, various other plasmid backbones are likely to be suitable. Thus, the invention is not to be limited by the illustrative embodiments described above. Instead, the invention is to be judged by the claims which follow.

What is claimed is:

1. A recombinant plasmid, comprising:
   a segment from a first plasmid which is not a lymphotrophic herpes virus segment and which facilitates the replication of the recombinant plasmid in a prokaryotic host;
   a segment from a lymphotrohic herpes virus which is linked to said first plasmid segment such that it is capable of assisting in maintaining the recombinant plasmid as a plasmid if the recombinant plasmid is inserted into a eukaryotic host that has been transformed by the lymphotrophic herpes virus; and
   a foreign eukaryotic gene component linked as part of the recombinant plasmid.

2. The recombinant plasmid of claim 1, wherein the foreign eukaryotic gene component is not a lymphotrophic herpes virus gene.

3. The recombinant plasmid of claim 2, wherein the lymphotrophic herpes virus segment is from Epstein-Barr virus.

4. The recombinant plasmid of claim 2, further comprising:
   a second gene segment from the lymphotrophic herpes virus, said second gene segment normally acting in trans to the first lymphotrophic herpes gene segment in the naturally occurring virus, whereby both the first and second lymphotrophic herpes virus gene segments assist the recombinant plasmid in maintaining itself as a plasmid if the recombinant plasmid is inserted in a eukaryotic host, even when the host has not been transformed by the virus.

5. The recombinant plasmid of claim 4, wherein both of said lymphotrophic herpes virus segments are from Epstein-Barr virus.

6. A eukaryotic host comprising:
   a recombinant plasmid having a segment from a first plasmid which is not a lymphotrophic herpes virus and which facilitates replication of the recombinant plasmid in a prokaryotic host, a segment from a lymphotrophic herpes virus which is linked to said first plasmid segment such that it is capable of assisting in maintaining the recombinant plasmid as a plasmid if the eukaryotic host has been transformed by the lymphotrophic herpes virus, and a foreign eukaryotic gene component linked as part of the recombinant plasmid; and
   a second gene segment from the lymphotrophic herpes virus which is not linked to the recombinant plasmid, said second lymphotrophic herpes virus gene segment normally acting in trans to the first lymphotrophic herpes virus gene segment in the naturally occurring virus, whereby both the first and second lymphotrophic herpes virus gene segments assist the recombinant plasmid in maintaining itself as a plasmid.

7. The eukaryotic host of claim 6, wherein both lymphotrophic herpes virus gene segments are from Epstein-Barr virus, and said trans portion codes for EBNA protein.

8. The eukaryotic host of claim 7, wherein the foreign eukaryotic gene is not a lymphotrophic herpes virus.

* * * * *